US008834849B2

(12) United States Patent
Millar

(10) Patent No.: US 8,834,849 B2
(45) Date of Patent: *Sep. 16, 2014

(54) MEDICINAL AEROSOLS AND METHODS OF DELIVERY THEREOF

(75) Inventor: Fiona Catherine Millar, Waterford (IE)

(73) Assignee: Norton Healthcare Limited, London (GB)

( * ) Notice: Subject to any disclaimer, the term of this patent is extended or adjusted under 35 U.S.C. 154(b) by 329 days.

This patent is subject to a terminal disclaimer.

(21) Appl. No.: 12/455,236

(22) Filed: May 29, 2009

(65) Prior Publication Data

US 2009/0246148 A1    Oct. 1, 2009

Related U.S. Application Data

(63) Continuation of application No. 08/999,752, filed on Jun. 4, 1997, now Pat. No. 7,566,445.

(30) Foreign Application Priority Data

Aug. 1, 1996 (GB) .................................. 9616237.5

(51) Int. Cl.
*A61K 9/12* (2006.01)
*A61K 9/14* (2006.01)
*A61K 9/00* (2006.01)

(52) U.S. Cl.
CPC ...................................... *A61K 9/008* (2013.01)
USPC ................... 424/45; 424/46; 424/47; 424/489

(58) Field of Classification Search
None
See application file for complete search history.

(56) References Cited

U.S. PATENT DOCUMENTS

| | | | |
|---|---|---|---|
| 2,868,691 A | 1/1959 | Porush et al. | |
| 3,014,844 A | 12/1961 | Thiel et al. | |
| 4,814,161 A | 3/1989 | Jinks et al. | |
| 4,895,719 A | 1/1990 | Radhakrishnan et al. | |
| 5,115,803 A * | 5/1992 | Sioutas | 128/200.23 |
| 5,118,494 A | 6/1992 | Schultz et al. | |
| 5,225,183 A | 7/1993 | Purewal et al. | |
| 5,348,730 A | 9/1994 | Greenleaf et al. | |
| 5,355,872 A * | 10/1994 | Riggs et al. | 128/200.21 |
| 5,376,359 A | 12/1994 | Johnson | |
| 5,605,674 A | 2/1997 | Purewal et al. | |
| 5,653,961 A | 8/1997 | McNally et al. | |
| 5,653,962 A | 8/1997 | Akehurst et al. | |
| 5,674,471 A | 10/1997 | Akehurst et al. | |
| 5,695,743 A | 12/1997 | Purewal et al. | |
| 5,766,573 A | 6/1998 | Purewal et al. | |
| 5,891,419 A | 4/1999 | Cutie | |
| 5,899,201 A * | 5/1999 | Schultz et al. | 128/200.23 |
| 5,980,867 A * | 11/1999 | Tzou et al. | 424/45 |
| 6,004,537 A | 12/1999 | Blondino et al. | |
| 6,136,294 A | 10/2000 | Adjei et al. | |
| 6,261,539 B1 | 7/2001 | Adjei et al. | |
| 6,352,684 B1 | 3/2002 | Purewal et al. | |
| 6,458,338 B1 | 10/2002 | Adjei et al. | |
| 6,475,467 B1 | 11/2002 | Keller et al. | |
| 6,585,958 B1 | 7/2003 | Keller et al. | |
| 7,566,445 B1 | 7/2009 | Millar | |

FOREIGN PATENT DOCUMENTS

| | | |
|---|---|---|
| AT | 215359 | 4/2002 |
| AU | 3038197 | 2/1998 |
| CA | 2320129 | 6/1993 |
| CA | 2261879 | 2/1998 |
| CN | 1296814 | 5/2001 |
| DE | 19924098 | 12/2000 |
| DK | 918507 | 7/2002 |
| EP | 0372777 | 6/1990 |
| EP | 372777 | 6/1990 |
| EP | 0536235 | 4/1993 |
| EP | 0616525 | 9/1994 |
| EP | 0653205 | 5/1995 |
| EP | 0717987 | 6/1996 |
| EP | 0918507 | 6/1999 |
| EP | 1086688 | 3/2001 |
| ES | 2175413 | 11/2002 |
| JP | 7080069 | 3/1995 |
| JP | 200-515536 | 11/2000 |
| NO | 999454 | 3/1999 |
| NZ | 333986 | 5/1999 |
| WO | WO-9111173 | 8/1991 |
| WO | WO-9111495 | 8/1991 |
| WO | WO-9114422 | 10/1991 |
| WO | WO-9200062 | 1/1992 |
| WO | WO-9200107 | 1/1992 |
| WO | WO-9206675 | 4/1992 |
| WO | WO-9208446 | 5/1992 |
| WO | WO-9202287 | 12/1992 |
| WO | WO-9222286 | 12/1992 |

(Continued)

OTHER PUBLICATIONS

The Merck Index, 11th Edition, Merck & Co., Inc., Whitehouse Station, NJ, 1989, cover page + p. 663-664.
Merck Index, Ninth Edition, 1976, p. 30.
Ranucci, J.A et al., Pharmaceutical Technology Mar. 1992.
Clark, A.R., Journal of Biopharmaceutical Sciences, 3(1/2), 069-076 (1992).
James B. Fink, Respiratory Care, Jun. 2000, vol. 45: No. 6, pp. 623-635.
ABPI compendium of data sheets and summaries of product characteristics 1996-97, pa 566-567.

(Continued)

*Primary Examiner* — Susan Tran
(74) *Attorney, Agent, or Firm* — RatnerPrestia

(57) ABSTRACT

The replacement of chlorofluorohydrocarbon propellants in medical aerosols is of the utmost importance to the pharmaceutical industry. A number of formulations have been investigated.
The present invention provides a medical aerosol formulation comprising a particular medicament, a fluorocarbon propellant and 6 to 25% w/w of the total formulation of a polar co-solvent, such formulation being substantially free of surfactant. Canisters suitable for delivering such a pharmaceutical formulation are also provided.

6 Claims, No Drawings

(56) References Cited

FOREIGN PATENT DOCUMENTS

| WO | WO-9222288 | 12/1992 |
|----|----|----|
| WO | WO-9305765 | 4/1993 |
| WO | WO-9306185 | 4/1993 |
| WO | WO-9311743 | 6/1993 |
| WO | WO-9311744 | 6/1993 |
| WO | WO-9311745 | 6/1993 |
| WO | WO-9311747 | 6/1993 |
| WO | WO 9311747 A1 * | 6/1993 |
| WO | WO-9403153 | 2/1994 |
| WO | WO-9413262 | 6/1994 |
| WO | WO-9413263 | 6/1994 |
| WO | WO-9517195 | 6/1995 |
| WO | WO-9606598 | 3/1996 |
| WO | WO-9618384 | 6/1996 |
| WO | WO-9619198 | 6/1996 |
| WO | WO-9629985 | 10/1996 |
| WO | WO-9632345 | 10/1996 |
| WO | WO-9744012 | 11/1997 |
| WO | WO-9747286 | 12/1997 |
| WO | WO-9805302 | 2/1998 |
| WO | WO-9824420 | 6/1998 |
| WO | WO-9834595 | 8/1998 |
| WO | WO-9834596 | 8/1998 |
| WO | WO-9856349 | 12/1998 |
| WO | WO-9929296 | 6/1999 |
| WO | WO-9953901 | 10/1999 |
| WO | WO-9965460 | 12/1999 |
| WO | WO-9965464 | 12/1999 |
| WO | WO-0045795 | 8/2000 |
| WO | WO-0048587 | 8/2000 |
| WO | WO-0051591 | 9/2000 |
| WO | WO-0053187 | 9/2000 |
| WO | WO-0053188 | 9/2000 |
| WO | WO-0073170 | 12/2000 |

OTHER PUBLICATIONS

MIMS Jul. 1996, p. 220.
Extract from MIMS of Mar. 2007, 2 pages—D25 from Opposition of European Patent Application No. 97925141.0.
Complaints System dated Jul. 3, 1995, 1 page—D18d from Opposition of European Patent Application No. 97925141.0.
Aerosol adapter and spray, 1 page—D18c (submitted in Opposition on Jul. 15, 2006) from Opposition of European Patent Application No. 97925141.0.
Mrs. K. Kennedy, Letter from Medicines Control Agency, Mar. 10, 1995, 43 pages—D18b from Opposition of European Patent Application No. 97925141.0.
Barbara Moore, 3M Letter Re: Airomir Inhaler, Apr. 21, 2005, 1 page—D18a from Opposition of European Patent Application No. 97925141.0.
Extract from Ivax website, Oct. 1, 2001, 2 pages—D26 from Opposition of European Patent Application No. 97925141.0.
Email from MHRA to Dr. Furlong, Mar. 28, 2007, 2 pages—D27 from Opposition of European Patent Application No. 97925141.0.
Email correspondence between Dr. Furlong and the MHRA, Feb. 27, 2007, 8 pages—D24 from Opposition of European Patent Application No. 97925141.0.

* cited by examiner

MEDICINAL AEROSOLS AND METHODS OF DELIVERY THEREOF

CROSS-REFERENCE TO RELATED APPLICATIONS

This application is a continuation of U.S. application Ser. No. 08/999,752, filed on Jun. 4, 1997, the disclosure of which is incorporated herein by reference.

BACKGROUND OF THE INVENTION

This invention relates to pharmaceutical formulations for inhalation aerosols. The Montreal Protocol on ozone depleting gases has made the reformulation of existing pharmaceutical aerosols. for inhalation treatment containing chlorofluorohydrocarbon propellants, a matter of urgency for the pharmaceutical industry.

DETAILED DESCRIPTION

A number of hydrofluorocarbons (HFCs) have been the subject to toxicological testing and two in particular P134a (1,1,1,2-tetrafluoroethane) and P227 (1,1,1,2,3,3,3-heptafluoropropane) have been identified as safe for use in pharmaceutical aerosols.

A number of patent applications have been submitted in this field, the first being EP 372777, which discloses the use of four component mixtures, comprising a medicament, a surfactant, P134a and a co-solvent of higher polarity than the P134a, in the form of a solution or a suspension.

As inhalation aerosols are meant for administration to the lung, it has long been accepted that such formulations should contain as few ingredients as possible, to avoid putting unnecessary materials into the lung.

Historically, despite EP 372777, solution aerosols contained only medicament, propellant or propellant mixtures and, if necessary, co-solvent, usually ethanol, eg U.S. Pat. No. 2,868,691. The use of a surfactant was normally unnecessary for solution aerosols. However, historically medicinal suspension aerosols have contained a surfactant eg U.S. Pat. No. 3,014,844, as it was considered that the use of a surfactant was necessary to prevent agglomeration of particles, to prevent adhesion to the sides of the canister, and to aid valve lubrication and prevent valve sticking.

However it was disclosed in EP 616525 that it is possible to prepare medicament suspensions in a hydrofluorocarbon without the need for a surfactant, if a polar co-solvent was added. The normal co-solvent ethanol, has well established physiological actions and being a pure absorbable liquid eliminates any possibility of residues remaining in the lung. Irritation or possible toxicity from the surfactant, many of which are mixtures of similar compounds, are avoided.

EP 616525 specifically limits the polar co-solvent level to 0.01 to 5% w/w and in particular states (page 3, line 55) that the preferred level is about 0.1% w/w.

According to a first aspect of the present invention there is provided a medicinal aerosol formulation comprising a particulate medicament, a fluorocarbon propellant and 6%s to 25% w/w of the total formulation of a polar co-solvent, such formulation being substantially free of surfactant.

According to a second aspect of the present invention there is provided a medicinal aerosol formulation, comprising one or more particulate medicaments, one or more fluorocarbon or hydrocarbon or aliphatic gas propellants and 6% to 25% w/w of a polar co-solvent.

According to a third aspect of the present invention there is provided a canister suitable for delivering a pharmaceutical aerosol formulation, which comprises a container capable of withstanding the vapor pressure of the propellant used, which container is closed with a metering valve and contains a pharmaceutical aerosol formulation which comprises particulate medicament, a propellant consisting all or part of fluorocarbon and 6% to 25% of a polar co-solvent, which is substantially free of surfactant.

It has now been surprisingly found that higher levels of alcohol have beneficial results. Levels of 6% or more of ethanol produce satisfactory suspensions, which do not agglomerate on standing, and on reshaking produce finely dispersed medicament. It is believed that the higher levels of alcohol reduce the degree of deposition on the inside of the can. This is a very desirable feature. In addition, the use of these larger percentages of ethanol enables a much cheaper production process.

Medicinal aerosols can be filled either with one dose of liquid containing all of the ingredients mixed together or by a two dose process where the first dose contains the medicament and all other ingredients, including co-solvents, surfactants, if any, ancillary compounds eg flavors, if any, and some times some of the propellant followed by a second dose of pure propellant. This two dose fill has major cost advantages in that the volume of mix for a fixed number of cans is significantly smaller enabling the use of smaller mixing vessels. In particular, with the use of the new HFC propellants, which have lower boiling points than the old CFC propellants, the use of a one dose fill may involve the use of cooled pressurized vessels to prevent evaporation of the propellant gas during mixing and filling. With the new formulations with added extra co-solvent a first mix of just medicament suspended in the co-solvent can be used, followed by a second dose of pure propellant. This means that the propellant can be dosed directly from a holding tank into the can without any need to mix and store with the other ingredients. For example a mix weight of 1 g of medicament and co-solvent can be followed by 7.5 g of propellant. In this way the volume to be mixed is reduced from 8.5 g to 1 g. All the examples in EP 616525 are of laboratory scale, where the handling problems are much easier, but all the formulations described are such that it would not be practicable to fill in two doses without mixing the propellant, as is the case with the present disclosure.

The description of the filling method given on page 5 lines 2-13 indicates that only a one dose filling method is envisaged.

In all cases of the present invention the medicament consists of a particle size suitable for inhalation into the lung and will thus be less than 100 microns, desirably less than 20 microns and preferably in the range of 1-10 microns, normally with a mean particle size 1-5 microns.

Medicaments which may be administered in aerosol formulations according to the invention include any drug useful in inhalation therapy which may be presented in a form which is substantially completely insoluble in the selected propellant.

Appropriate medicaments may thus be selected from, for example, analgesics, eg codeine, dihydromophine, ergotamine, fentanyl or morphine; anginal preparations, eg diltiazem; antiallergics, eg cromoglycate, ketotifen or nedocromil; anti-infectives, eg cephalosporins, penicillins, streptomycin, sulphonamides, tetracyclines and pentamidine; antihistamines, eg methapyrilene; anti-inflammatories, eg beclomethasone, flunisolide, budesonide, tipredane, triamcinolone acetonide or fluticasone; antitussives, eg noscapine; bronchodilators, eg ephedrine, adrenaline, fenoterol, formoterol, isoprenaline, metaproterenol, phenylephrine, phenylpropanolamine, pirbuterol, reproterol, rimiterol, salbutamol, salmeterol, terbutaline, isoetharine, tolubuterol, orciprenaline; diuretics, eg amiloride; anticholinergics, eg ipratropium, atropine or oxitropium; hormones, eg cortisone, hydrocortisone or prednisolone; xanthines, eg aminophylline, choline theophyllinate, lysine theophyllinate or theophylline; and therapeutic proteins and peptides, eg insulin or glucagon. It will be clear to a person skilled in the art that, where appropriate, the medicaments may be used in the form of salts (eg as alkali metal or amine salts or as acid addition salts) or as esters (eg lower alkyl esters) or as solvates (eg hydrates) to optimize the activity and/or stability of the medicament and/or to minimize the solubility of the medicament in the propellant.

Preferred are those compounds which are also substantially insoluble in the co-solvent. Particularly preferred as medicament is salbutamol either as base or as a salt and especially salbutamol sulphate.

Co-solvents may be selected from polar alcohols and polyols, particularly C2-C6 aliphatic alcohols and polyols, such as propylene glycol, and preferably ethanol. Levels of co-solvent will be between 6% and 25% w/w of the total canister content, preferably between 10-15% w/w of canister content.

The propellant may be a hydrofluorocarbon, particularly P134a or P227. Other hydrofluorocarbons or hydrocarbons or aliphatic gases (eg Dimethylether) may be added to modify the propellant characteristics as required.

The product is preferentially produced by weighing the active medicament and suspending it in the co-solvent. The appropriate amount of suspension is then dosed into the can, followed by a second dose of propellant or propellant mix. However, a one shot fill or any other equivalent method may be employed.

The normal medicinal product on the market has an actuator with spray orifice diameter of about 480 microns. However, with the larger percentages of ethanol envisaged in this invention, it is desirable that the co-solvent evaporates from the particles as rapidly as possible.

This is achieved by reducing the aperture to between 100-300 microns, which for the same dosage or drug, gives more rapid evaporation of the co-solvent. A particularly preferred embodiment of the invention is a combination of a level 10-15% co-solvent (normally ethanol) with a stem aperture of 150-250 microns.

The invention is further described by means of example but not in any limitative sense.

EXAMPLE

| Salbutamol Sulphate | 0.03 g |
|---|---|
| Ethanol | 0.97 g |
| Tetrafluoroethane (P134a) | 7.5 g |

The salbutamol sulphate previously micronized to give over 90% of particles below 10 microns was weighed out and added to the ethanol. The suspension was mixed until is was smooth and uniform and then filled into the aerosol canister. The metering valve assembly was crimped (preferably vacuum crimped) on the canister and then the P134a was filled through the valve. The valve capacity is such as to deliver 100 micrograms of salbutamol, as salbutamol sulphate per actuation.

A particularly preferred use of such a canister is in a patient breath operated device rather than the normal hand operated device. Such devices are available commercially such as those under the trade mark "Easi-Breathe".

The invention claimed is:

1. A product suitable for delivering a pharmaceutical aerosol formulation comprising,
    (a) an aerosol canister comprising a container closed with a metering valve, said container comprising a pharmaceutical suspension aerosol formulation substantially free of surfactant, and which comprises salbutamol sulphate, ethanol in an amount of 10% w/w to 15% w/w, and 1,1,1,2-tetrafluoroethane, wherein salbutamol sulphate is substantially completely insoluble in the 1,1,1,2-tetrafluoroethane, and
    (b) an actuator with a spray orifice aperture of from 100 to 300 microns.

2. The product of claim 1, wherein the aerosol formulation contains ethanol in the amount of 11.4% w/w.

3. The product of claim 1, wherein the aerosol formulation contains 1,1,1,2tetrafluoroethane in the amount of 88.2% w/w.

4. The product of claim 1, wherein the aerosol formulation contains salbutamol sulphate in the amount of 0.4% w/w, ethanol in the amount of 11.4% w/w, and 1,1,1,2-tetrafluoroethane in the amount of 88.2% w/w.

5. The product of claim 1, wherein the spray orifice aperture is from 150 to 250 microns.

6. The product of claim 5, wherein ethanol is present in the amount of 10% w/w to 15% w/w.

* * * * *

UNITED STATES PATENT AND TRADEMARK OFFICE
CERTIFICATE OF CORRECTION

PATENT NO. : 8,834,849 B2  Page 1 of 1
APPLICATION NO. : 12/455236
DATED : September 16, 2014
INVENTOR(S) : Fiona Catherine Millar It is certified that error appears in the above-identified patent and that said Letters Patent is hereby corrected as shown below:

In the Claims
Column 4, line 38, in Claim 3, 1,1,1,2tetrafluoroethane should read --1,1,1,2-tetrafluoroethane--.

Signed and Sealed this
Twenty-fourth Day of February, 2015

Michelle K. Lee
*Deputy Director of the United States Patent and Trademark Office*